United States Patent [19]

Wyatt, III et al.

[11] Patent Number: 5,760,306

[45] Date of Patent: Jun. 2, 1998

[54] PROBE HEAD ORIENTATION INDICATOR

[75] Inventors: Joseph Robert Wyatt, III; John Paul Sheppard, II, both of Lynchburg, Va.

[73] Assignee: Framatome Technologies, Inc., Lynchburg, Va.

[21] Appl. No.: 705,958

[22] Filed: Aug. 30, 1996

[51] Int. Cl.[6] .................................................. G01N 29/04
[52] U.S. Cl. .......................... 73/623; 73/40.5; 73/865.8
[58] Field of Search .......................... 73/40.5, 598, 620, 73/622, 623, 627, 628, 633, 637, 638, 644, 865:8

[56] References Cited

U.S. PATENT DOCUMENTS

| | | | |
|---|---|---|---|
| 3,810,384 | 5/1974 | Evans | 73/622 X |
| 3,994,173 | 11/1976 | Ward et al. | 73/432 |
| 4,131,018 | 12/1978 | Muller et al. | 73/432 |
| 4,361,044 | 11/1982 | Kupperman et al. | 73/623 |
| 4,581,938 | 4/1986 | Wentzell | 73/623 |
| 4,597,294 | 7/1986 | Brill, III et al. | 73/623 |
| 4,663,727 | 5/1987 | Saporito et al. | 364/551 |
| 4,772,849 | 9/1988 | Tedder | 324/220 |
| 4,805,459 | 2/1989 | Ferreira | 73/627 X |
| 4,856,337 | 8/1989 | Metala et al. | 73/601 |
| 4,856,354 | 8/1989 | Overbay | 73/886.5 |
| 4,964,059 | 10/1990 | Sugaya et al. | 364/507 |
| 5,070,734 | 12/1991 | Kawabuchi et al. | 73/628 |
| 5,248,940 | 9/1993 | Patience et al. | 73/660 X |
| 5,285,689 | 2/1994 | Hapstack et al. | 73/623 |
| 5,396,800 | 3/1995 | Drinon et al. | 73/623 |

*Primary Examiner*—Richard Chilcot
*Assistant Examiner*—Paul D. Amrozowicz
*Attorney, Agent, or Firm*—Rhodes Coats & Bennett, L.L.P.

[57] ABSTRACT

An apparatus for determining both the axial and angular positions of a defect in a tube wall. The apparatus includes a probe head positioned at the end of an elongated probe carrier having an imbedded orientation indicator. In the preferred embodiment, an encoder measures the angular orientation of the probe head when facing the defect relative to the angular orientation of the carrier and a photodetector and reflective strip measure the angular orientation of the carrier relative to a known orientation. A data processor uses this data to calculate the angular orientation of the probe head and the location of the tube defect.

46 Claims, 2 Drawing Sheets

PROBE HEAD ORIENTATION INDICATOR

BACKGROUND OF THE INVENTION

(1) Field of the Invention

The present invention relates generally to an apparatus for inspecting the interior of conduits or tubes and, more particularly, to an apparatus for determining both the axial and angular positions of detected defects in heat exchanger tubes such as found in a nuclear steam generator.

(2) Description of the Prior Art

Heat exchanger tubes in a nuclear steam generator used to generate electricity must be periodically inspected to detect corroded or thinning areas or other defects in the tubing walls, so that these areas can be repaired to prevent leakage. Usually detection is performed by inserting an inspection probe into the tubing. The probe includes a rotatable probe head positioned at the end of a tubular carrier through which electrical wiring connects the drive means and detector of the probe head to an external power source and controls. The probe head includes a detector, e.g., an ultrasonic detector, an eddy current detector, or both, which measures changes in wall conditions.

The axial position of the wall defect can be determined by measuring the distance that the probe head has been inserted into the tubing. However, knowing the angular position of the defect would be helpful in properly correcting the defect. In the prior art, attempts have been made to measure the angular position of a defect by positioning a field detection or field generating device in an adjacent boiler tube. Since the relative positions of the two tubes are known, measuring of the change in detection by the probe head during rotation shows the angular orientation of the probe head, and thus the angle of a monitored defect.

U.S. Pat. No. 5,396,800, issued to Drinon et al., discloses an apparatus and method for inspecting a tubular member for degradation. The apparatus includes a pusher/puller mechanism connected to a support body for simultaneously translating the support body, a bladder, a sensor, and a sleeve to actually scan the tube. As the support body is rotated and translated, the sleeve is stationary with respect to the sensor because the bladder secures the sleeve to the support body. Thus, as the support body and the sensor connected thereto are rotated and translated, the sleeve will be rotated and translated to a like extent. In this manner, the material properties of the sleeve are radially and axially invariant relative to the sensor for obtaining a more precise inspection of the tube.

U.S. Pat. No. 4,964,059, issued to Sugaya et al., discloses an apparatus for inspecting a pipeline having a pig body which measures an inner shape and a wall thickness of a pipe body. The apparatus includes a rotation angle gauge for measuring a rotation angle of the pig body about its center axis, a recorder for the pig body which stores measured data, and a signal processing device for processing signals from a distance measuring device, the rotation angle gauge and any defect detection transducers.

U.S. Pat. No. 4,663,727, issued to Saporito et al., discloses an ultrasonic inspection system for inspecting areas of tubular members and providing a display of any internal flaws therein. The inspection system utilizes a stepping motor on a scanner drive which drives a wand and a probe axially to a location just above an area to be inspected. A second stepping motor rotates the wand to enable the probe to perform a circumferential scan. The indexing and circumferential scanning proceeds until the entire area is scanned.

U.S. Pat. No. 4,856,354, issued to Overbay, discloses a manipulator for a fiberscope probe or other inspection probe. The manipulator includes a fixed base and a chassis rotating on a hollow spindle relative to the base. The chassis, spindle and an internal housing rotate together with a translative motor for powering a friction drive and a rotation providing motor. The rotation motor acts with a gear fixed relative to the base and is controlled through limit switches for 400° of rotation. A potentiometer monitors rotational positions.

Thus, there remains a need for a new and improved method and apparatus for measuring both the axial and angular positions of a probe head and thus a boiler wall defect towards which the probe head faces while, at the same time, not requiring the presence of a corresponding detector or signal generator in an adjacent tube.

SUMMARY OF THE INVENTION

The present invention is directed to an apparatus for determining the angular orientation of a probe head within a tube, such as a heat exchanger tube of a nuclear steam generator. The invention also relates to an apparatus for detecting and determining the angular position of defects in a tube. In addition, the invention relates to an apparatus for determining the angular position of a probe head supporting carrier.

The present invention determines the angular orientation of a probe head, and thereby a defect faced by the probe head, by measuring the angular orientation of the probe head when the probe head is facing the defect relative to the known position of a probe carrier inside the tube. Preferably, a probe carrier highly resistant to torsional flexing is used to minimize twisting of the carrier between the two areas where the measurements are made. Therefore, the two measurements can be used to determine the angular orientation of the probe head relative to a known position, and thus the location of the defect.

Various designs of probe heads may be used in the present apparatus, and in the practice of the present method. The probe head includes a defect sensor directed toward the tubing wall, a drive means for rotating the probe head, and a measurement means for determining the position of the probe head relative to an orientation indicator on the carrier.

Defect sensors known in the prior art, and suitable for use in the probe head of this invention include ultrasonic and eddy current sensors and combinations of these sensors. In an ultrasonic sensor, a transmitter directs ultrasonic sound waves against the tube wall, and a receiver detects changes in the reflected wave. An eddy current sensor detects changes in eddy currents emanating from a coil as a result of changes in the wall section toward which the sensor faces.

The rotation drive means preferably will be a small electric motor with a drive shaft geared to the probe head. The measurement means may be an encoder communicating with, and measuring the rotation of, the motor drive shaft. The encoder may be calibrated to zero when the defect sensor is facing a predetermined direction. Wiring providing electrical current to the motor from an external source, and wiring to transmit data from the measurement means to an externally located data processor extend from the probe head through the interior of the tubular carrier.

Preferably, the carrier used to support the probe head is in the form of an elongated, flexible tube of high torsional resistance comprised of a continuous outer wall with a remote end upon which the probe head is positioned. For reasons to be described in detail hereinafter, the carrier also includes an orientation indicator positioned on or in its outer wall. Preferably, the orientation indicator extends longitudinally along the wall, parallel to the carrier axis, to the remote end of the carrier.

The orientation detector assembly includes an annular rotor rotatable within a housing; a detector carried by the rotor; drive means, e.g., an electric motor, for rotating the rotor within the housing; and measurement means for measuring the position of the rotor, and thereby the defect sensor carried thereon relative to the housing. The measurement means may be an encoder connected to the drive shaft of the motor.

In order to measure the baseline position of the carrier, the orientation indicator assembly is positioned at a known orientation, and the carrier is inserted through the cylindrical opening of the tube. The rotor carrying the detector, is then rotated about the carrier wall. The detector employed is designed to detect the presence of the indicator on the carrier wall. For example, an eddy current coil may be used to detect the presence of an indicator comprised of a conductive wire positioned in or on the wall, so that a change in current is produced when the detector is oriented toward the wire. Alternatively, the detector may be a light source in combination with a photocell to detect changes in light intensity, and the indicator may be a longitudinal stripe that reflects light differently from the wall of the carrier, e.g., the wall may be light with a dark stripe, or the wall may be dark with a light stripe.

Data relating to changes in current resulting from detection of the indicator, and data relating to the position of the rotor and detector relative to the stationary housing, are transmitted to the data processor that also receives data from the probe head relating to the angular position of the probe head relative to the carrier. The data processor, which is of conventional design, then calculates the position of a tube wall defect from this data by combining the angular position of the measurement means with the position of the detector relative to the known location of the orientation indicator assembly.

Preferably, the indicator on the carrier wall extends longitudinally to the probe head, and the position of the detector at the probe head, as it rotates pass the indicator, is used as the zero point in calculating the position of the defect sensor on the probe head. In this event, this additional data is not required. Also, if the indicator extends to the probe head, the probe head can include a detector of the type used in the carrier position measurement means, and the angular difference between the position where the indicator is detected, and the position where the defect is detected can be used to calculate the angular position of the defect relative to the carrier.

Accordingly, one aspect of the present invention is to provide an apparatus for determining both the axial and angular positions of a defect in a tube. The apparatus includes: (a) a probe head including a defect sensor for detecting a defect in the wall of the tube; (b) a first drive means for axially positioning the probe head along the length inside the tube and providing the axial location of the probe head; (c) an angular orientation indicator for providing the angular position of the probe head, the orientation indicator including: (i) a carrier tube resistant to torsional flexing attached to the probe head having an indicator extending along the length of the carrier tube at a predetermined angular position and (ii) a detector for detecting the angular position of the indicator, thereby determining the angular position of the carrier tube and the probe head; and (d) data processor for combining the axial and angular positions to determine the position of the defect in the tube.

Another aspect of the present invention is to provide an angular orientation indicator for providing the angular position of a probe head. The orientation indicator includes: (a) a carrier tube resistant to torsional flexing attached to the probe head having an indicator extending along the length of the carrier tube at a predetermined angular position; and (b) a detector for detecting the angular position of the indicator, thereby determining the angular position of the carrier tube and the probe head;

Still another aspect of the present invention is to provide an apparatus for determining both the axial and angular positions of a defect in a tube. The apparatus including: (a) a probe head including a defect sensor for detecting a defect in the wall of the tube; (b) a first drive means for axially positioning the probe head along the length inside the tube and providing the axial location of the probe head; (c) an angular orientation indicator for providing the angular position of the probe head, the orientation indicator including: (i) a carrier tube resistant to torsional flexing attached to the probe head having an indicator extending along the length of the carrier tube at a predetermined angular position and (ii) a detector for detecting the angular position of the indicator, thereby determining the angular position of the carrier tube and the probe head; (d) a second drive means for rotating the probe head with respect to the carrier tube and providing the angular orientation of the probe head with respect to the indicator of the carrier tube when the defect sensor is facing a defect in the tube; and (e) data processor for combining the axial and angular positions to determine the position of the defect in the tube.

These and other aspects of the present invention will become apparent to those skilled in the art after a reading of the following description of the preferred embodiment when considered with the drawings.

DESCRIPTION OF THE PREFERRED EMBODIMENTS

Figure 1:
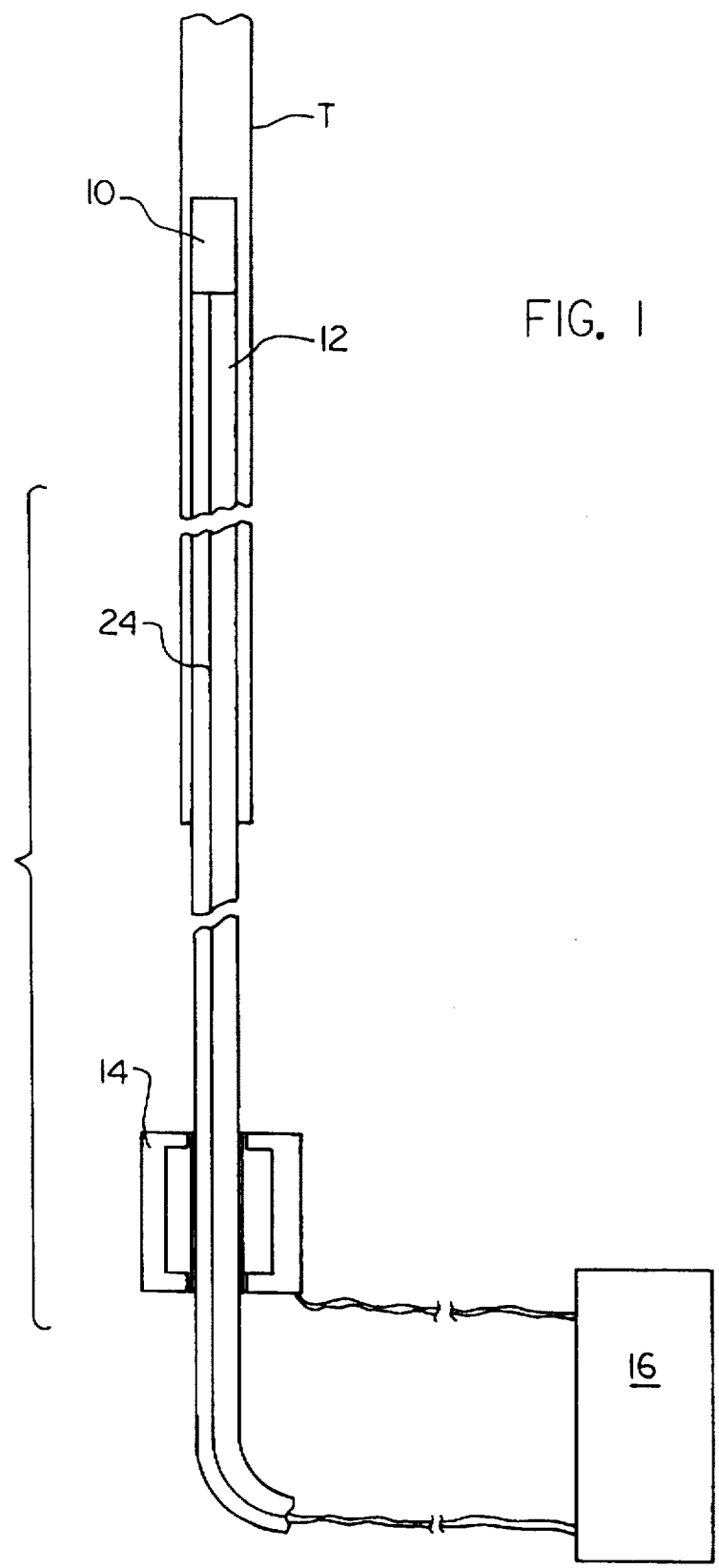
FIG. 1 is a schematic view of a probe orientation indicator constructed according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, the apparatus of the present invention includes a rotatable probe head 10 carried on the end of an elongated tubular carrier 12, the probe head and carrier having a diameter less than the internal diameter of tube T to be inspected. It is to be understood that tube T is one of a number of tubes positioned inside a steam generator.

Carrier 12 extends through orientation detector 14 that can be stationarily positioned at various locations for convenience in use, with the orientation of orientation detector 14 being in a given direction.

Probe head 10 and orientation detector 14 are wired to data processor 16 for transmittal of measurement data to processor 16 for calculation of the probe head angular orientation to determine the defect position.

Figure 2:
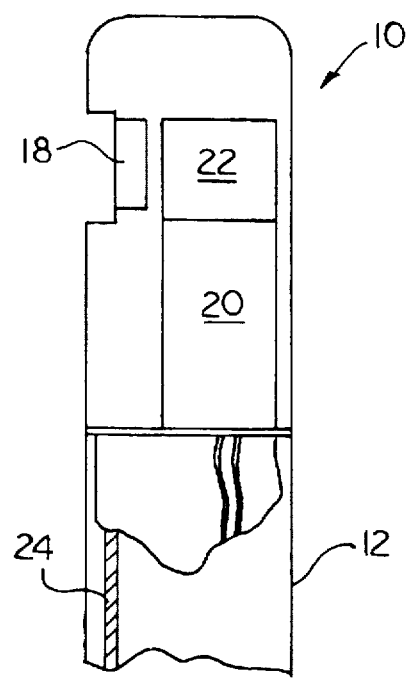
FIG. 2 is a detailed view of the probe head and a section of the carrier.

Probe head 10, best shown in FIG. 2, includes outwardly directed, defect sensor 18, drive motor 20 to rotate probe head 10, and encoder 22 communicating with motor 20. Probe head 10 is rotatably positioned at the end of carrier 12, which includes indicator 24, shown in the preferred embodiment as a black stripe on a white carrier wall. Encoder 22 is set to zero when defect sensor 18 is aligned with indicator 24.

Defect sensor 18 is an ultrasonic detector with a transmitter to direct ultrasonic sound waves against the interior wall of tube T, and a receiver to detect changes in the reflected waves. An eddy current detector can be substituted for the ultrasonic detector.

Figure 3:
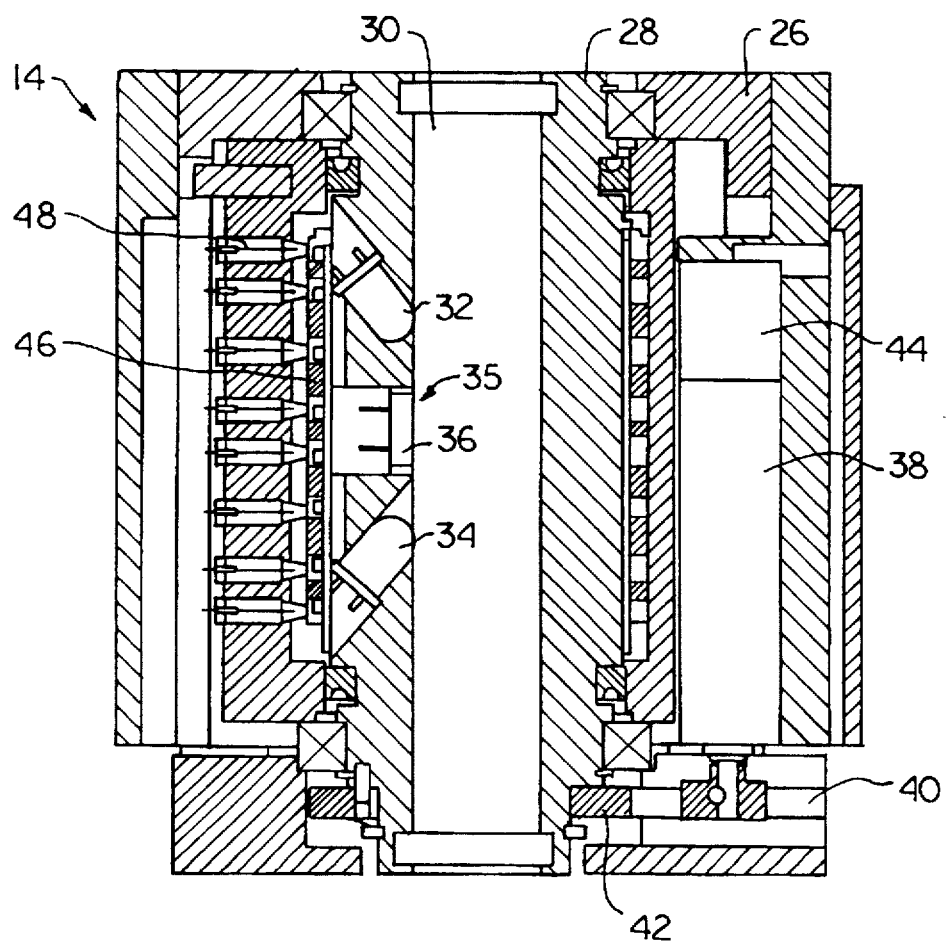
FIG. 3 is a sectional side view of the orientation indicator assembly.

Orientation detector 14, shown in detail in FIG. 3, includes housing 26 and rotor 28 rotatably mounted within housing 26. Rotor 28 includes a vertically oriented, cylindrical opening 30 therethrough. Detector 35, carried by rotor 28, includes LED light sources 32 and 34 positioned to direct light against the wall of carrier 12 within cylinder 30, and photosensor 36 positioned to measure the intensity of light reflected from the wall of carrier 12.

Electric motor 38, mounted in housing 26, is geared to rotor 28 by motor pinion 40 and stator gear 42 to rotate rotor 28 within housing 26. Encoder 44 is positioned on motor 38, and is connected to the drive shaft of motor 38 to measure the shaft position, and thereby the position of rotor 28 relative to housing 26. Thus, the position of detector 35, and thereby carrier indicator 24 is known when a change in light intensity, recorded as a change in current, is detected by detector 35.

Electrical connections between housing 26 and rotor 28 are by way of conductive rings 46 positioned on rotor 28, engagable by brushes 48 positioned on housing 26.

In operation, orientation detector 14 is mounted at a desired location, such as on existing inspection equipment and manipulator tooling, and is oriented to a known angular position. Carrier 12 is inserted through cylindrical opening 30, with probe head 10 being inserted into tube T. Carrier 12 may be moved upwardly or downwardly through cylinder 30 to axially position probe head 10 at the desired height in tube T. Rotor 28 with detector 35 carried thereon, is then rotated about carrier 12 by drive motor 38. Light sources 32 and 34 illuminate the wall of carrier 12, and light is reflected onto photosensor 36, which measures the light intensity.

When a change in light intensity is detected by photosensor 36, indicating the presence of the indicator, the change is transmitted to data processor 16 as a change in current. At the same time, data processor 16 records the position of rotor 28 and detector 35, as determined by encoder 44. Data processor 16 then determines the angular orientation of the carrier relative to the known position based on this data.

Data can be collected from the carrier orientation detector 14 and a calculation of the carrier orientation can be made without data from the probe head encoder. However, if the angular orientation of a rotating probe head is to be determined, data collected from the carrier orientation detector is combined with data from the probe head.

Preferably, a probe carrier highly resistant to torsional flexing is used to minimize twisting of the carrier between the two areas where the measurements are made. Initial measurements have determined that plastic tubing having a durometer of greater than about D80 will perform satisfactory. In addition, for a typical 5/16 inch diameter carrier tube, a wall thickness of more than about 1/16 inches is sufficiently resistant to torsional flexing for meaningful measurements.

Certain modifications and improvements will occur to those skilled in the art upon a reading of the foregoing description. By way of example, while imbedded wire and reflective and non-reflective stripes are preferred carrier indicators, other types of indicators such as grooves and magnetic stripes could possibly be utilized. It should be understood that all such modifications and improvements have been deleted herein for the sake of conciseness and readability but are properly within the scope of the following claims.

We claim:

1. An angular orientation indicator for providing the angular position of a probe head, said orientation indicator comprising:

(a) a carrier tube resistant to torsional flexing attached to said probe head having an indicator extending along the length of said carrier tube at a predetermined angular position; and (b) a detector for detecting the angular position of said indicator, thereby determining the angular position of said carrier tube and said probe head, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position.

2. The apparatus according to claim 1, wherein said detector is an eddy current detector and said indicator is a conductive wire.

3. The apparatus according to claim 1, wherein said detector is a photosensor and said indicator is a stripe having a light reflectance different from said wall.

4. The apparatus according to claim 1, further including a rotor around said conduit.

5. The apparatus according to claim 4, further including a housing around said rotor, said housing being positionable in a predetermined angular orientation.

6. The apparatus according to claim 5, wherein said rotor includes conductive rings and said housing includes brushes engaging said rings to transfer electrical current between said housing and said rotor to power said detector.

7. The apparatus according to claim 1, wherein said measurement means is an encoder.

8. The apparatus according to claim 1, wherein said means for rotating said detector around said conduit is an electric motor having a drive shaft, and said measurement means is connected to said drive shaft.

9. An apparatus for determining both the axial and angular positions of a defect in a tube, said apparatus comprising:

(a) a probe head including a defect sensor for detecting a defect in the wall of said tube;

(b) a first drive means for axially positioning said probe head along the length inside said tube and providing the axial location of said probe head;

(c) an angular orientation indicator for providing the angular position of said probe head, said orientation indicator including:

(i) a carrier tube resistant to torsional flexing attached to said probe head having an indicator extending along the length of said carrier tube at a predetermined angular position and (ii) a detector for detecting the angular position of said indicator, thereby determining the angular position of said carrier tube and said probe heads, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position;

(d) a second drive means for rotating said probe head with respect to said carrier tube and providing the angular orientation of said probe head with respect to said indicator of said carrier tube when said defect sensor is facing a defect in said tube; and (e) data processor for combining said axial and angular positions to determine the position of said defect in said tube.

10. The apparatus according to claim 9, wherein said defect sensor is an ultrasonic detector.

11. The apparatus according to claim 9, wherein said defect sensor is an eddy current detector.

12. The apparatus according to claim 9, wherein said detector is an eddy current detector and said indicator is a conductive wire.

13. The apparatus according to claim 9, wherein said detector is a photosensor and said indicator is a stripe having a light reflectance different from said wall.

14. The apparatus according to claim 9, further including a rotor around said conduit.

15. The apparatus according to claim 14, further including a housing around said rotor, said housing being positionable in a predetermined angular orientation.

16. The apparatus according to claim 15, wherein said rotor includes conductive rings and said housing includes brushes engaging said rings to transfer electrical current between said housing and said rotor to power said detector.

17. The apparatus according to claim 9, wherein said measurement means is an encoder.

18. The apparatus according to claim 9, wherein said means for rotating said detector around said conduit is an electric motor having a drive shaft, and said measurement means is connected to said drive shaft.

19. An angular orientation indicator for providing the angular position of a probe head, said orientation indicator comprising:

(a) a carrier tube resistant to torsional flexing attached to said probe head having an indicator extending along the length of said carrier tube at a predetermined angular position; and (b) a detector for detecting the angular position of said indicator, thereby determining the angular position of said carrier tube and said probe head, wherein said detector is an eddy current detector and said indicator is a conductive wire.

20. The apparatus according to claim 19, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position.

21. The apparatus according to claim 20, further including a rotor around said conduit.

22. The apparatus according to claim 21, further including a housing around said rotor, said housing being positionable in a predetermined angular orientation.

23. The apparatus according to claim 22, wherein said rotor includes conductive rings and said housing includes brushes engaging said rings to transfer electrical current between said housing and said rotor to power said detector.

24. The apparatus according to claim 20, wherein said measurement means is an encoder.

25. The apparatus according to claim 20, wherein said means for rotating said detector around said conduit is an electric motor having a drive shaft, and said measurement means is connected to said drive shaft.

26. An angular orientation indicator for providing the angular position of a probe head, said orientation indicator comprising:

(a) a carrier tube resistant to torsional flexing attached to said probe head having an indicator extending along the length of said carrier tube at a predetermined angular position; and (b) a detector for detecting the angular position of said indicator, thereby determining the angular position of said carrier tube and said probe head, wherein said detector is a photosensor and said indicator is a stripe having a light reflectance different from said wall.

27. The apparatus according to claim 24, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position.

28. The apparatus according to claim 27, further including a rotor around said conduit.

29. The apparatus according to claim 28, further including a housing around said rotor, said housing being positionable in a predetermined angular orientation.

30. The apparatus according to claim 29, wherein said rotor includes conductive rings and said housing includes brushes engaging said rings to transfer electrical current between said housing and said rotor to power said detector.

31. The apparatus according to claim 27, wherein said measurement means is an encoder.

32. The apparatus according to claim 27, wherein said means for rotating said detector around said conduit is an electric motor having a drive shaft, and said measurement means is connected to said drive shaft.

33. An apparatus for determining both the axial and angular positions of a defect in a tube, said apparatus comprising:

(a) a probe head including a defect sensor for detecting a defect in the wall of said tube;

(b) a first drive means for axially positioning said probe head along the length inside said tube and providing the axial location of said probe head;

(c) an angular orientation indicator for providing the angular position of said probe head, said orientation indicator including: (i) a carrier tube resistant to torsional flexing attached to said probe head having an indicator extending along the length of said carrier tube at a predetermined angular position and (ii) a detector for detecting the angular position of said indicator, thereby determining the angular position of said carrier tube and said probe head, wherein said detector is an eddy current detector and said indicator is a conductive wire;

(d) a second drive means for rotating said probe head with respect to said carrier tube and providing the angular orientation of said probe head with respect to said indicator of said carrier tube when said defect sensor is facing a defect in said tube; and (e) data processor for combining said axial and angular positions to determine the position of said defect in said tube.

34. The apparatus according to claim 33, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position.

35. The apparatus according to claim 34, further including a rotor around said conduit.

36. The apparatus according to claim 35, further including a housing around said rotor, said housing being positionable in a predetermined angular orientation.

37. The apparatus according to claim 36, wherein said rotor includes conductive rings and said housing includes brushes engaging said rings to transfer electrical current between said housing and said rotor to power said detector.

38. The apparatus according to claim 34, wherein said measurement means is an encoder.

39. The apparatus according to claim 34, wherein said means for rotating said detector around said conduit is an electric motor having a drive shaft, and said measurement means is connected to said drive shaft.

40. An apparatus for determining both the axial and angular positions of a defect in a tube, said apparatus comprising:

(a) a probe head including a defect sensor for detecting a defect in the wall of said tube;

(b) a first drive means for axially positioning said probe head along the length inside said tube and providing the axial location of said probe head;

(c) an angular orientation indicator for providing the angular position of said probe head, said orientation indicator including: (i) a carrier tube resistant to torsional flexing attached to said probe head having an indicator extending along the length of said carrier tube at a predetermined angular position and (ii) a detector for detecting the angular position of said indicator, thereby determining the angular position of said carrier tube and said probe head, wherein said detector is a photosensor and said indicator is a stripe having a light reflectance different from said wall;

(d) a second drive means for rotating said probe head with respect to said carrier tube and providing the angular orientation of said probe head with respect to said indicator of said carrier tube when said defect sensor is facing a defect in said tube; and (e) data processor for combining said axial and angular positions to determine the position of said defect in said tube.

41. The apparatus according to claim 40, wherein said detector includes a tubular conduit having a known predetermined angular position and adapted to receive said carrier tube, said detector facing said conduit to detect the presence of said indicator on said carrier tube; means for rotating said detector around said conduit; and measurement means to determine the angular position of said detector relative to said predetermined angular position.

42. The apparatus according to claim 41, further including a rotor around said conduit.

43. The apparatus according to claim 42, further including a housing around said rotor, said housing being positionable in a predetermined angular orientation.

44. The apparatus according to claim 43, wherein said rotor includes conductive rings and said housing includes brushes engaging said rings to transfer electrical current between said housing and said rotor to power said detector.

45. The apparatus according to claim 41, wherein said measurement means is an encoder.

46. The apparatus according to claim 41, wherein said means for rotating said detector around said conduit is an electric motor having a drive shaft, and said measurement means is connected to said drive shaft.

* * * * *

UNITED STATES PATENT AND TRADEMARK OFFICE
CERTIFICATE OF CORRECTION

PATENT NO. : 5,760,306
DATED : June 2, 1998
INVENTOR(S) : Joseph Robert Wyatt, III et al.

It is certified that error appears in the above-indentified patent and that said Letters Patent is hereby corrected as shown below:

Column 7,

In Claim 9, Section (c)(i), Line 5, after the word probe, "heads" should be --head--.

Signed and Sealed this

Eighteenth Day of August, 1998

Attest:

BRUCE LEHMAN

*Attesting Officer*          *Commissioner of Patents and Trademarks*